United States Patent
Lotvall et al.

(10) Patent No.: US 11,561,223 B2
(45) Date of Patent: Jan. 24, 2023

(54) METHOD AND SYSTEM FOR IDENTIFYING MEMBRANE PROTEINS ON EXTRACELLULAR VESICLES

(71) Applicant: Exocure Biosciences Inc., San Diego, CA (US)

(72) Inventors: Jan Lotvall, Boston, MA (US); Su Chul Jang, Boston, MA (US); Aleksander Cvjetkovic, Gothenburg (SE); Cecilia Lasser, Gothenburg (SE)

(73) Assignee: Exocure Biosciences Inc., San Diego, CA (US)

( * ) Notice: Subject to any disclaimer, the term of this patent is extended or adjusted under 35 U.S.C. 154(b) by 392 days.

(21) Appl. No.: 16/641,906

(22) PCT Filed: Sep. 17, 2018

(86) PCT No.: PCT/EP2018/075105
§ 371 (c)(1),
(2) Date: Feb. 25, 2020

(87) PCT Pub. No.: WO2019/053274
PCT Pub. Date: Mar. 21, 2019

(65) Prior Publication Data
US 2020/0249234 A1 Aug. 6, 2020

(30) Foreign Application Priority Data
Sep. 15, 2017 (GB) ...................... 1714890

(51) Int. Cl.
*G16B 40/10* (2019.01)
*G01N 33/574* (2006.01)
*G01N 33/68* (2006.01)

(52) U.S. Cl.
CPC ... *G01N 33/57415* (2013.01); *G01N 33/6848* (2013.01); *G16B 40/10* (2019.02);
(Continued)

(58) Field of Classification Search
CPC ......... G01N 33/57415; G01N 33/6848; G01N 2333/912; G01N 2560/00;
(Continued)

(56) References Cited

U.S. PATENT DOCUMENTS 9,149,542 B2   10/2015   Gho et al.
9,220,763 B2   12/2015   Gho et al.
(Continued)

FOREIGN PATENT DOCUMENTS

EP   2617413 A2   7/2013
EP   3251659 A1   12/2017
(Continued)

OTHER PUBLICATIONS

Coumans et al., (2017) "Methodological guidelines to study extracellular Vesicles", Circ. Res., 120(10):1632-1648.
(Continued)

*Primary Examiner* — Michael Maskell
(74) *Attorney, Agent, or Firm* — Bozicevic, Field & Francis LLP; Shweta Chandra

(57) ABSTRACT

Disclosed is a method of isolating extracellular vesicles and identifying membrane proteins therefrom. The method includes providing human plasma and/or serum; separating lipoproteins and extracellular vesicles from the human plasma and/or serum by a density gradient preparation, collecting the extracellular vesicles from the separated lipoproteins and extracellular vesicles; isolating and purifying the collected extracellular vesicles by using size exclusion chromatography; treating the isolated and purified extracellular vesicles with an aqueous solution to obtain membranes of the extracellular vesicles, wherein the aqueous solution has a pH in a range of 9 to 14; adding salt in a concentration range between 0.5-2.0M to the aqueous solution; isolating the membranes from the treated extracellular vesicles and
(Continued)

identifying proteins on the isolated membranes by employing mass spectrometry.

11 Claims, 9 Drawing Sheets

(52) U.S. Cl.
CPC ... *G01N 2333/912* (2013.01); *G01N 2560/00* (2013.01); *G01N 2800/7028* (2013.01)

(58) Field of Classification Search
CPC ..... G01N 2800/7028; G01N 33/57488; G01N 33/5091; G01N 33/6803; G01N 33/6842; G16B 40/10
USPC ........................................ 250/281, 282, 288
See application file for complete search history.

(56) References Cited

U.S. PATENT DOCUMENTS

| | | | |
|---|---|---|---|
| 11,333,665 B2* | 5/2022 | Lotvall | ............ G01N 33/56977 |
| 2008/0207723 A1 | 8/2008 | Kopreski | |
| 2015/0086639 A1 | 3/2015 | Huang | |
| 2015/0218254 A1 | 8/2015 | Sabbadini et al. | |
| 2016/0061842 A1 | 3/2016 | Di Vizio | |
| 2018/0036240 A1 | 2/2018 | Gho et al. | |
| 2018/0296483 A1 | 10/2018 | Gho et al. | |
| 2018/0318409 A1 | 11/2018 | Valiante et al. | |
| 2022/0080035 A1 | 3/2022 | Park et al. | |

FOREIGN PATENT DOCUMENTS

| | | | |
|---|---|---|---|
| EP | 2450032 B1 | 9/2018 | |
| WO | 2009051427 | 4/2009 | |
| WO | WO2009130649 | 10/2009 | |
| WO | WO2010010983 | 1/2010 | |
| WO | 2010056337 | 5/2010 | |
| WO | WO-2010056337 A2 * | 5/2010 | ........... C12Q 1/6806 |
| WO | 2010070124 | 6/2010 | |
| WO | 2013063439 | 5/2013 | |
| WO | WO2015085096 | 6/2015 | |
| WO | 2016136372 | 9/2016 | |
| WO | WO2017161010 | 9/2017 | |
| WO | WO2017205810 | 11/2017 | |
| WO | WO2018171947 | 9/2018 | |

OTHER PUBLICATIONS

Karimi et al., (2018) "Detailed analysis of the plasma extracellular vesicle proteome after separation from lipoproteins", Cell. Mol. Life Sci., 75(15):2873-2886.
Jeppesen et al., (2014) "Quantitative proteomics of fractionated membrane and lumen exosome proteins from isogenic metastatic and nonmetastatic bladder cancer cells reveal differential expression of EMT factors", Proteomics (14)6:699-712.
Mariantonia et al., (2009) "High levels of exosomes expressing CD63 and caveolin-1 in plasma of melanoma patients. e5219", Plos One, 4(4):1-10.
Matsushita et al., (1989) "Effect of Extracellular pH on the Respiratory Chain and Energetics of Gluconobacter suboxydans", Agricultural and Biological Chemistry,53(11):2895-2902.
Shin et al., (2015) "High-yield isolation of extracellular vesicles using aqueous two-phase system", Scientific Reports, (5)1:1-11.
Tauro et al., (2012) "Two Distinct Populations of Exosomes Are Released from LIM1863 Colon Carcinoma Cell-derived Organoids", Molecular & Cellular Proteomics, 12(3):587-598.
Yoshioka et al., (2014) "Ultra-sensitive liquid biopsy of circulating extracellular vesicles using ExoScreen". Nature Communications, (5)3591:1-8.
U.S. Appl. No. 17/642,140, filed Mar. 10, 2022.
U.S. Appl. No. 17/731,833, filed Apr. 28, 2022.

* cited by examiner

METHOD AND SYSTEM FOR IDENTIFYING MEMBRANE PROTEINS ON EXTRACELLULAR VESICLES

TECHNICAL FIELD

The present disclosure generally relates to methods and systems for isolating extracellular vesicles from plasma and/or serum and identifying membrane proteins, in particular methods and systems for purification of extracellular vesicles and identifying breast cancer specific-membrane proteins obtained from tissues of a patient. Furthermore, the present disclosure also relates to software products recorded on machine-readable non-transient data storage media, wherein the software products are executable upon computing hardware to implement the aforesaid method of profiling membrane proteins.

BACKGROUND

Extracellular vesicles (EVs) are known to be released by various cells in human bodies. Specifically, extracellular vesicles are nano-sized vesicles (40 nm to 1000 nm in diameter) with a lipid bi-layer membrane; for example, extracellular vesicles (EVs) include microvesicles, apoptotic bodies, ectosomes and exosomes. Generally, extracellular vesicles mediate intercellular communication by activating surface receptors of recipient cells. Alternatively, cargo proteins, nucleic acids (such as DNAs, mRNAs, siRNAs, miRNAs, and small non-coding RNAs) or lipids may be transferred to the recipient cells to facilitate intercellular communication. Beneficially, a cargo of the extracellular vesicles may be protected, from extracellular enzymes and immune system operation, by a lipid membrane bilayer. Furthermore, the extracellular vesicles include membrane proteins in the lipid membrane bilayer.

Typically, extracellular vesicles are found in bodily fluids such as blood (plasma and serum), urine, saliva, cerebrospinal fluid, semen, ascites, synovial fluid, bronchoalveolar lavage, pleural effusion, amniotic fluid, sweats, feces, cystic fluids, tears and breast milk. Furthermore, extracellular vesicles carry signatures of cells that produce them.

Conventionally, extracellular vesicles may function as diagnostic biomarkers that may be used for detecting specific diseases. However, such methods are complex and time-intensive. Furthermore, disease-specific membrane proteins may be isolated (or, purified) from the extracellular vesicles for diagnosis of diseases. However, isolation of disease-specific membrane proteins is difficult and isolated (namely, purified) membrane proteins may not be substantially pure. Therefore, membrane protein characteristics, such as intensity and quantity of membrane proteins, may not be accurate. Furthermore, the membrane proteins profiles created using such isolated membrane proteins may not yield accurate or desired outcome or result.

Therefore, in light of the foregoing discussion, there exists a need to overcome the aforementioned drawbacks associated with conventional profiling of membrane proteins.

SUMMARY

It is an object of the present disclosure to provide a new methodology of isolating extracellular vesicles and identifying membrane proteins therefrom.

A further objective of the present disclosure is to use the membrane proteins profiles in identification of biomarkers associated with breast cancer.

These and other objects, which are evident to the skilled person from the present disclosure, are met by the different aspects of the invention as claimed in the appended claims and as generally disclosed herein.

According to a first aspect, the invention is realized by a method of isolating extracellular vesicles and identifying membrane proteins therefrom, characterized in that the method comprises steps of:
  (a) providing human plasma and/or serum;
  (b) separating lipoproteins and extracellular vesicles from the human plasma and/or serum by a density gradient preparation;
  (c) collecting the extracellular vesicles from the separated lipoproteins and extracellular vesicles;
  (d) isolating and purifying the collected extracellular vesicles by using size exclusion chromatography;
  (e) treating the isolated and purified extracellular vesicles with an aqueous solution to obtain membranes of the extracellular vesicles, wherein the aqueous solution has a pH in a range of 9 to 14;
  (f) adding salt in a concentration range between 0.5-2.0M to the aqueous solution;
  (g) isolating the membranes from the treated extracellular vesicles; and
  (h) identifying proteins on the isolated membranes by employing mass spectrometry.

The above defined method enables profiling of membrane proteins obtained from tissues of a patient and to identify corresponding membrane protein signatures for further analysis and biomarker discovery. All cells in vivo produce the extracellular vesicles, and those extracellular vesicles are to a great extent entrapped in extracellular matrix of tissues. The released vesicles from any cell, or from any tissue, include a cloud of vesicles with different content, membrane molecules and with cellular origin. This makes the extracellular vesicles attractive biomarker sources.

Optionally, the method further comprises a step:
  (i) ultracentrifugation of the human plasma and/or serum to concentrate extracellular vesicles therein, wherein the step (i) is performed before the step (b).

According to a second aspect, the invention is realized by a method of identifying breast cancer specific-membrane proteins, characterized in that the method comprises steps of:
  (a) isolating extracellular vesicles from tissues of patients;
  (b) identifying membrane proteins associated with the isolated extracellular vesicles by mass spectrometry;
  (c) comparing membrane proteins derived from extracellular vesicles of breast cancerous tissues with membrane proteins identified at step (g) of claim 1 by specifically subtracting the membrane proteins from plasma and/or serum, to identify tissue and/or disease-specific membrane proteins;
  (d) creating membrane proteins profiles for the identified disease-specific membrane protein;
  (e) plotting the created membrane proteins profiles of the patient against pre-determined membrane proteins profiles of healthy tissues and cancerous tissues; and
  (f) comparing expressional differences in breast cancerous tissues derived extracellular vesicles membrane proteins with membrane proteins derived from extracellular vesicles of the plasma and/or serum.

Optionally, at the step (a) of isolating the extracellular vesicles, the method includes:
  (i) slicing the tissues into fragments;
  (ii) incubating the fragments with one or more enzymes to release the extracellular vesicles; and
  (iii) centrifuging the incubated fragments for segregating tissue debris and the extracellular vesicles.

More optionally, the one or more enzymes are selected from a group of proteases including a matrix metalloproteinase, collagenases, and papain and nucleases including DNase, RNase, and Benzonase.

Optionally, at the step (e) comparing the created membrane proteins profiles of the sample tissues against the pre-determined membrane proteins profiles of the healthy tissues and cancerous tissues is performed by employing at least one of a nanoFCM analysis, ELISA, alphaLISA, FACS, fluorescent correlation microscopy and immune-electron microscopy.

More optionally, the method further comprises a step of:
(g) isolating the extracellular vesicles from body fluids before the step (a).

Optionally, the breast cancer-specific membrane protein is Receptor tyrosine-protein kinase erbB-2 and/or Cytoskeleton-associated protein 4.

According to a third aspect, the invention is realized by a system for identifying biomarkers for breast cancer using healthy plasma and carcinogenic breast tissues, characterized in that the system includes:
(a) a mass spectrometer for recognizing disease-specific membrane proteins from extracellular vesicles derived membrane proteins for sample breast tissue/s of a breast cancer suspect and for recognizing membrane proteins of extracellular vesicles from healthy plasma;
(b) a quantifying arrangement for quantifying the recognized disease-specific membrane proteins to identify a major disease specific membrane protein; and
(c) a computing unit for
    (i) creating membrane proteins profiles for the identified major disease-specific membrane protein, and
    (ii) comparing the created membrane proteins profiles of the sample breast tissues against pre-determined membrane proteins profiles of the healthy plasma and the carcinogenic breast tissues.

Optionally, the computing unit includes memory stored with executable codes operable to:
(i) search the recognized disease-specific membrane proteins in respect of a pre-existing database of protein sequences;
(ii) identify the major disease-specific membrane proteins for each group of the recognized disease-specific membrane proteins;
(iii) obtain intensity information relating to the major disease-specific membrane proteins by employing a label-free quantification tool or an isotope labelling-based quantification tool; and
(iv) compare expressional differences in breast cancerous tissues derived extracellular vesicles membrane proteins with membrane proteins derived from extracellular vesicles of the plasma and/or serum.

Optionally, comparing is performed by employing at least one of a nanoFCM analysis, ELISA, alphaLISA, FACS, fluorescent correlation microscopy and immune-electron microscopy.

According to a fourth aspect, the invention is realized by a kit for capturing extracellular vesicles and detecting breast cancer-associated markers, characterized in that the kit comprises:
(a) an epitope specific binder against breast cancer-associated membrane proteins; and
(b) at least one breast cancer-associated marker detection agent According to a fifth aspect, the invention is realized by a computer program product comprising non-transitory computer-readable storage medium having computer-readable instructions stored thereon, the computer-readable instructions being executable by a computerized device comprising processing hardware to execute the aforesaid methods.

It will be appreciated that features of the invention are susceptible to being combined in various combinations without departing from the scope of the invention as defined by the appended claims.

A better understanding of the present invention may be obtained through the following examples which are set forth to illustrate, but are not to be construed as limiting the present invention.

BRIEF DESCRIPTION OF THE DRAWINGS

Embodiments of the present disclosure will be more fully understood from examples described herein below and the accompanying drawings, which is given by way of illustration only, and thus are not limitative of the present invention, and wherein.

Figure 1:
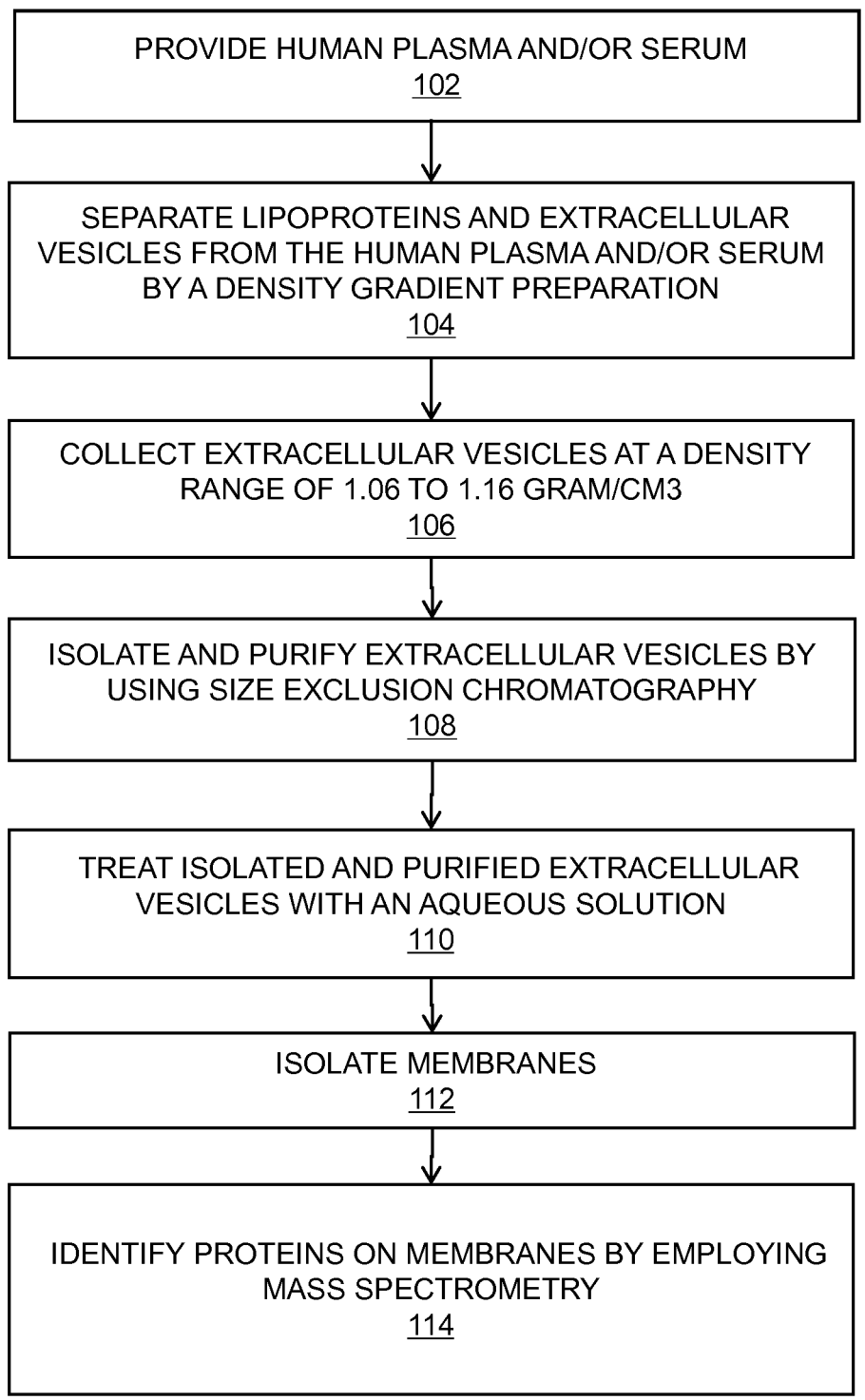
FIG. 1 is an illustration of steps of a method of isolating extracellular vesicles and identifying membrane proteins therefrom, in accordance with an embodiment of the present disclosure.

In the accompanying diagrams, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

LIST OF ABBREVIATIONS

Abbreviation Meaning
EVs Extracellular vesicles mm
Millimeter
DNase Deoxyribonuclease RPMI medium Roswell Park Memorial Institute medium
μm Micrometre
g Gravitational constant ml Milliliter
PBS Phosphate-buffered saline
MS Mass spectrometry
LC-MS Liquid chromatography-mass spectrometry
FASP Filter-aided sample preparation
SDS Sodium dodecyl sulphate
TEAB Tetra-ethyl-ammonium bromide nL
Normal liters
Min. Minute
HCD Higher energy collisional dissociation
Ppm Parts per-million moles
PE Signals Pulsed electroacoustic signals
LFQ Label free quantification

DEFINITIONS

As used herein, the following terms shall have the following meanings:

As used herein, the term "extracellular vesicle" means a vesicle released by a cell. Examples of "extracellular vesicles" include exosomes, ectosomes, microvesicles, prostasomes, oncosomes, and apoptotic bodies.

The term "membrane" means biological membranes, i.e. the outer coverings of cells and organelles that allow passage of certain compounds. The term "membrane" typically refers to an extracellular vesicle or organelle which encloses an intravesicular or organellar content and which has been opened to provide a non-enclosing form of the extracellular vesicle or organelle, i.e. a membrane form. Such membrane may originate from the outer Cell membrane, the Golgi-apparatus, the Endoplasmic reticulum, the nucleus or mitochondria.

The terms "cell media", "culture media" and/or "cell culture media" as used herein refer to a culture media used for preserving or culturing human cancer tissues, cells and/or cell lines obtained from patient during surgery. The culture media include all supplements required for culturing and preservation of carcinoma cell lines. The culture media may not include fetal bovine serum. For example, if the sample is a solid sample, cells from the sample can be cultured and an exosome product is induced. In some embodiments, the sample is ascites fluid from a subject, e.g., ascites fluid from a human subject with ovarian cancer; cell culture media supernatant from a human primary melanoma cell line; cell culture mediasupernatant from a human primary colon cancer cell line; or murine macrophage, e.g., murine macrophage infected with tuberculosis. The culture media may be an ordinary medium, or may also be liquid nitrogen based medium. The liquid medium can be isotonic, hypotonic, or hypertonic. In certain embodiments, the liquid medium contains a buffer and/or at least one salt or a combination of salts. Buffers can maintain pH within a particular range, for example, between 1 and 12, and are also referred to as pH stabilizing agents.

The term "membrane protein(s)" as used herein refers to proteins that interact with, or are part of, biological membranes of EVs. The membrane proteins may include, but are not limited to, integral membrane proteins and peripheral membrane proteins.

The term "disease specific membrane proteins" as used herein refers to membrane proteins that code for a specific disease. The disease specific membrane proteins may individually code for a disease, alternatively a group of disease specific membrane proteins may code for a disease.

The term "apoptotic-body" as used herein refers to degenerate basal epidermal cells. The apoptotic bodies may include, but are not limited to, colloid, hyaline, filamentous and/or civattebodies. Furthermore, the apoptotic bodies may be round, shrunken, homogeneous, eosinophilic bodies in the stratum basale.

The term "conjugated antibody" as used herein refers to a monoclonal or polyclonal antibody linked to a label and used for detection in a diverse range of assay techniques. The conjugated antibody may include, but is not limited to, linking with proteins of high molecular weight.

The term "profiling" as used herein refers to identifying intensity related information of the disease specific membrane proteins and plotting the intensity related information of disease specific membrane proteins in respect of the intensity related information of the membrane proteins derived from healthy tissues and cancerous tissues. The term profiling may also relate to identifying a biomarker associated with breast cancer.

DETAILED DESCRIPTION

The practice of the embodiments described in further detail below will employ, unless otherwise indicated, conventional methods of diagnostics, molecular biology, cell biology, biochemistry and immunology within the skill of the art. Such techniques are explained fully in the literature.

It is appreciated that certain features of the invention, which are for clarity described in the context of separate embodiments, may also be provided in combination in a single embodiment. Conversely various features of the invention which are for brevity described in the context of a single embodiment, may also be provided separately and/or in any suitable sub-combination.

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

As illustrated in FIG. 1, there are shown steps of a method 100 of isolating extracellular vesicles and identifying membrane proteins therefrom, in accordance with an embodiment of the present disclosure. At a step 102, human plasma and/or serum is provided for isolation of extracellular vesicles. At a step 104, lipoproteins and extracellular vesicles are separated from the human plasma and/or serum by a density gradient preparation. At a step 106, the extracellular vesicles are collected from the separated lipoproteins and extracellular vesicles. At a step 108, the extracellular vesicles are further isolated and purified by using size exclusion chromatography. At a step 110, extracellular vesicles are treated with an aqueous solution of pH in a range of 9 to 14 for obtaining membranes of the extracellular vesicles. At a step 112, a salt in a concentration range between 0.5-2.0M is added to the aqueous solution. At a step 114 the membranes are isolated and at a step 116, proteins on the membranes of plasma and/or serum extracellular vesicles are identified by employing mass spectrometry.

Optionally, the method 100 may further include a step of ultracentrifugation prior to the step 104 for separating the lipoproteins and extracellular vesicles from the human plasma and/or serum by a density gradient preparation.

In an embodiment, at the step 106 of the method 100, the extracellular vesicles may be collected at a density range of 1.06 to 1.16 g/cm$^3$ of the density gradient preparation.

Figure 2:
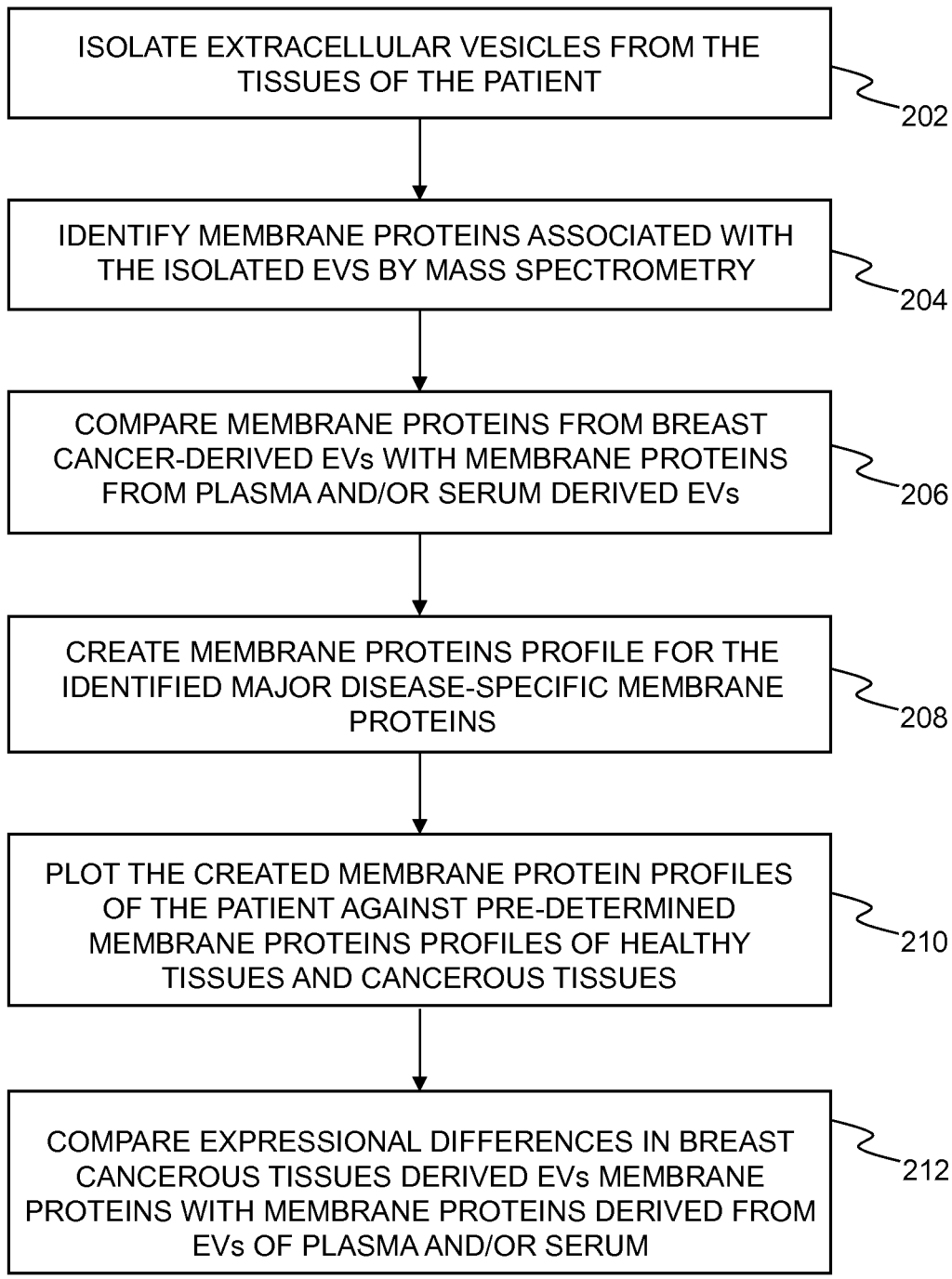
FIG. 2 is an illustration of steps of a method of identifying breast cancer specific-membrane proteins, in accordance with an embodiment of the present disclosure.

As illustrated in FIG. 2, there are shown steps of a method 200 of identifying breast cancer specific-membrane proteins, in accordance with an embodiment of the present disclosure. At a step 202, extracellular vesicles are isolated from the tissues of the patient. At a step 204, membrane proteins associated with the isolated extracellular vesicles are identified by employing mass spectrometry. At a step 206, the membrane proteins derived from extracellular vesicles of breast cancerous tissues are compared with membrane proteins derived from extracellular vesicles of plasma and/or serum by subtracting the membrane proteins from plasma and/or serum, to identify tissue and/or disease-specific membrane proteins. At a step 208, membrane proteins profiles are created for the identified major disease-specific membrane proteins. At a step 210, the created membrane protein profiles of the patient are plotted against pre-determined membrane proteins profiles of healthy tissues and cancerous tissues. At a step 212, expressional differences in breast cancerous tissue derived extracellular vesicles membrane proteins are compared against the membrane proteins derived from extracellular vesicles of plasma and/or serum.

Optionally, the step 202 for isolating the extracellular vesicles includes slicing the tissues into fragments, incubating the fragments with one or more enzymes to release the extracellular vesicles and centrifuging the incubated fragments for segregating tissue debris and the extracellular vesicles. In an embodiment, incubating the fragments of the tissues may be performed in presence of one or more enzymes selected from a group of proteases including a matrix metalloproteinase, collagenases, and papain and nucleases including DNase, RNase, and Benzonase. Moreover, the step 202 may include filtration of the incubated tissues fragments.

Optionally, the method 200 includes employing a Protein Assay for identifying the membrane proteins associated with the isolated extracellular vesicles.

Optionally, the method 200 includes quantifying the recognized disease-specific membrane proteins to identify the major disease-specific membrane protein may include searching the recognized disease-specific membrane proteins in respect of a pre-existing database of protein sequences, identifying the major disease-specific membrane proteins for each group of the recognized disease-specific membrane proteins, and obtaining intensity information relating to the major disease-specific membrane proteins by employing a label-free quantification tool or an isotope labeling-based quantification tool. For example, searching the recognized disease-specific membrane proteins may be performed on the basis of at least one parameter including an enzyme specificity, a variable modification, a fixed modification, oxidation properties, carbamidomethylation properties and an ion tolerance. Moreover, the information relating to the intensity of the major disease-specific membrane proteins may include, but is not limited to, the concentration and/or sequence lengths of the major disease-specific membrane proteins.

Optionally, at the step 210 comparing the created membrane proteins profiles of the sample tissues against the pre-determined membrane proteins profiles of the healthy tissues and cancerous tissues employs a nanoFCM analysis, ELISA, alphaLISA, FACS, fluorescent correlation microscopy, immune-electron microscopy, or other methods detecting membrane proteins on the EVs. The nanoFCM analysis is performed for plotting the created membrane protein profiles of the patient against pre-determined membrane proteins profiles of healthy tissues and cancerous tissues.

According to an embodiment, the method 200 may include creating pre-determined membrane proteins profiles of healthy tissues and cancerous tissues. For example, the method 200 may include isolating extracellular vesicles from the healthy and cancerous tissues, identifying the membrane proteins associated with the isolated extracellular vesicles, and quantifying the identified membrane proteins for creating the pre-determined membrane proteins profiles of healthy tissues and cancerous tissues.

Optionally, the method 200 may include an additional step of isolating the extracellular vesicles from body fluids before the step 202 of isolating the extracellular vesicles.

Optionally, the breast cancer-specific membrane proteins may include at least one of Receptor tyrosine-protein kinase erbB-2 and/or Cytoskeleton-associated protein 4.

In an embodiment, the method 200 includes isolating EVs from tissues of the patient using a centrifugation based protocol. For example, tumor pieces (i.e. tissues) are sliced in fragments and incubated in RPMI plain medium for 30 minutes at 37° C. The RPMI plain medium contains collagenase D having a concentration of 2 mg/ml and DNase I having a concentration of 2 U/ml. After incubation, filtration of suspension culture of the fragments is performed and cell debris are eliminated or segregated by centrifugation. Furthermore, the suspension culture of the fragments is re-centrifuged for collecting small and large EVs. The larger and smaller EVs are isolated at lower speed (16,500×g) and at higher speed (118,000×g), respectively. Larger EVs are 100-200 nm in diameter and have an RNA profile comparable to microvesicles (MVs)—a subpopulation of EVs that are considered to be produced by membrane budding. In contrast, smaller EVs are 40-100 nm in diameter and exhibited RNA profiles similar to exosomal RNA profiles, without prominent ribosomal RNA peaks. The collected EVs are suspended in a PBS solution for disengaging cells clumped with the aforementioned small and large EVs. Furthermore, the aforementioned small and large EVs are purified by an isopycnic centrifugation. The purified EVs are suspended in a 1% PBS mixed with 60% iodixanol, followed by an ultracentrifugation for extracting membrane proteins from the EVs. Furthermore, a Protein Assay is applied for identifying and quantifying the extracted membrane proteins.

Figure 3:
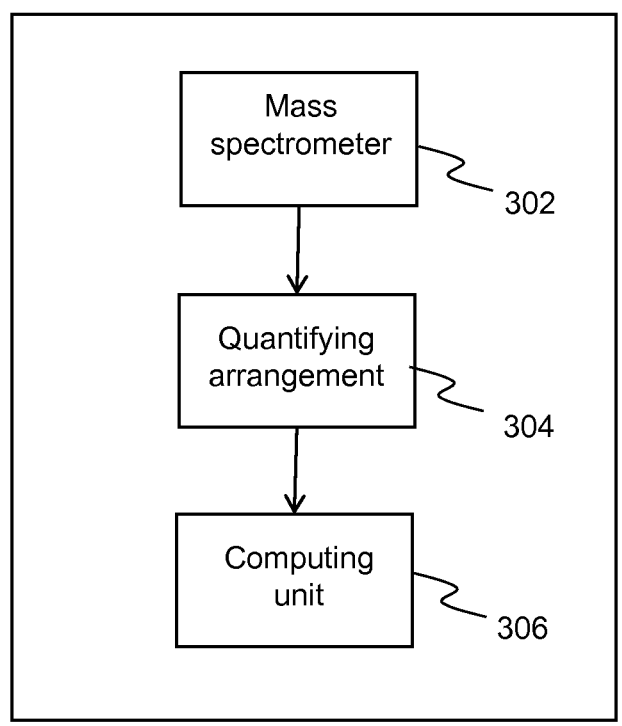
FIG. 3 is a block diagram of a system for identifying biomarkers for breast cancer using healthy plasma and carcinogenic breast tissues, in accordance with an embodiment of the present disclosure.

Referring to FIG. 3, there is illustrated a system 300 for identifying biomarkers for breast cancer using healthy plasma and carcinogenic breast tissues, in accordance with an embodiment of the present disclosure. The system 300 includes a mass spectrometer 302, a quantifying arrangement 304 and a computing unit 306. The mass spectrometer 302 of the system 200 is operable, namely configured, to recognize disease-specific membrane proteins from the identified membrane proteins. The quantifying arrangement 304 is operable, namely configured, to quantify the recognized disease-specific membrane proteins to identify a major disease-specific membrane protein. The quantifying arrangement 304 is operationally associated with the computing unit 306, and the computing unit 306 is operable to create membrane proteins profiles for the identified major disease-specific membrane proteins and operable to plot the created membrane proteins profiles of the patient against pre-determined membrane proteins profiles of healthy tissues and cancerous tissues.

Optionally, the system 300 includes an isolating arrangement, and an identifying arrangement. The isolating arrangement of the system 300 may be operable, namely configured, to isolate extracellular vesicles from the tissues of the patient and connected with the identifying arrangement. The identifying arrangement of the system 300 may be operable, namely configured, to identify the membrane proteins associated with the isolated extracellular vesicles.

Optionally, the system 300 includes at least one slicer for slicing the tissues into fragments, at least one incubator for incubating the fragments with one or more enzymes to release the extracellular vesicles, and at least one centrifuge for segregating tissue debris and the extracellular vesicles from the incubated fragments. In an example, incubation of the fragments of the tissues may be performed in a presence of one or more enzymes selected from a group of proteases including a matrix metalloproteinase, collagenases, and papain and nucleases including DNase, RNase, and Benzonase. Optionally, the isolating arrangement of the system 300 may include a filtration arrangement for separating tissue debris and the extracellular vesicles from centrifuged suspension of the incubated fragments.

In an embodiment, the identifying arrangement of the system 300 may include employing a Protein Assay for identifying the membrane proteins associated with the isolated extracellular vesicles.

Optionally, the mass spectrometer 302 of the system 300 may be used for separating the membrane proteins and the disease-specific membrane proteins. In an example, the quantification arrangement 304 of the system 300 may be operable, namely configured, to employ a Protein Assay for quantifying the recognized disease-specific membrane proteins to identify a major disease-specific membrane protein.

In one embodiment, the computing unit 306 of the system 300 may include a data memory stored with executable codes. Furthermore, the computing unit 306 may be operable, namely configured, to search the recognized disease-specific membrane proteins in respect of a pre-existing database of protein sequences, to identify the major disease-specific membrane proteins for each group of the recognized disease-specific membrane proteins, to obtain intensity information relating to the major disease-specific membrane proteins by employing a label-free quantification tool or an isotope labeling-based quantification tool and to compare expressional differences in tumor-derived extracellular vesicles membrane proteins from tumor tissues against plasma or serum extracellular vesicles membrane proteins. For example, the computing system 306 may perform a search on a basis of at least one parameter including enzyme specificity, a variable modification, a fixed modification, oxidation properties, carbamidomethylation properties and an ion tolerance. Furthermore, the information relating to the intensity of the major disease-specific membrane proteins may include, but is not limited to, the concentration and/or sequence lengths of the major disease-specific membrane proteins.

In an embodiment, the computing unit 306 may be operable, namely configured, to employ a nanoFCM analysis, ELISA, alphaLISA, FACS, fluorescent correlation microscopy, immune-electron microscopy, or other methods, for comparing expressional differences in tumor-derived extracellular vesicles membrane proteins from tumor tissues against plasma or serum extracellular vesicles membrane proteins.

Optionally, the system 300 may be operable, namely configured, to create pre-determined membrane proteins profiles of healthy tissues and cancerous tissues. For example, the isolating arrangement may be operable, namely configured, to isolate extracellular vesicles from the healthy and cancerous tissues, and the identifying arrangement may be operable, namely configured, to identify the membrane proteins associated with the isolated extracellular vesicles. Furthermore, the quantifying arrangement 304 may be operable, namely configured, to quantify the identified membrane proteins by employing the Protein Assay.

Figure 4:
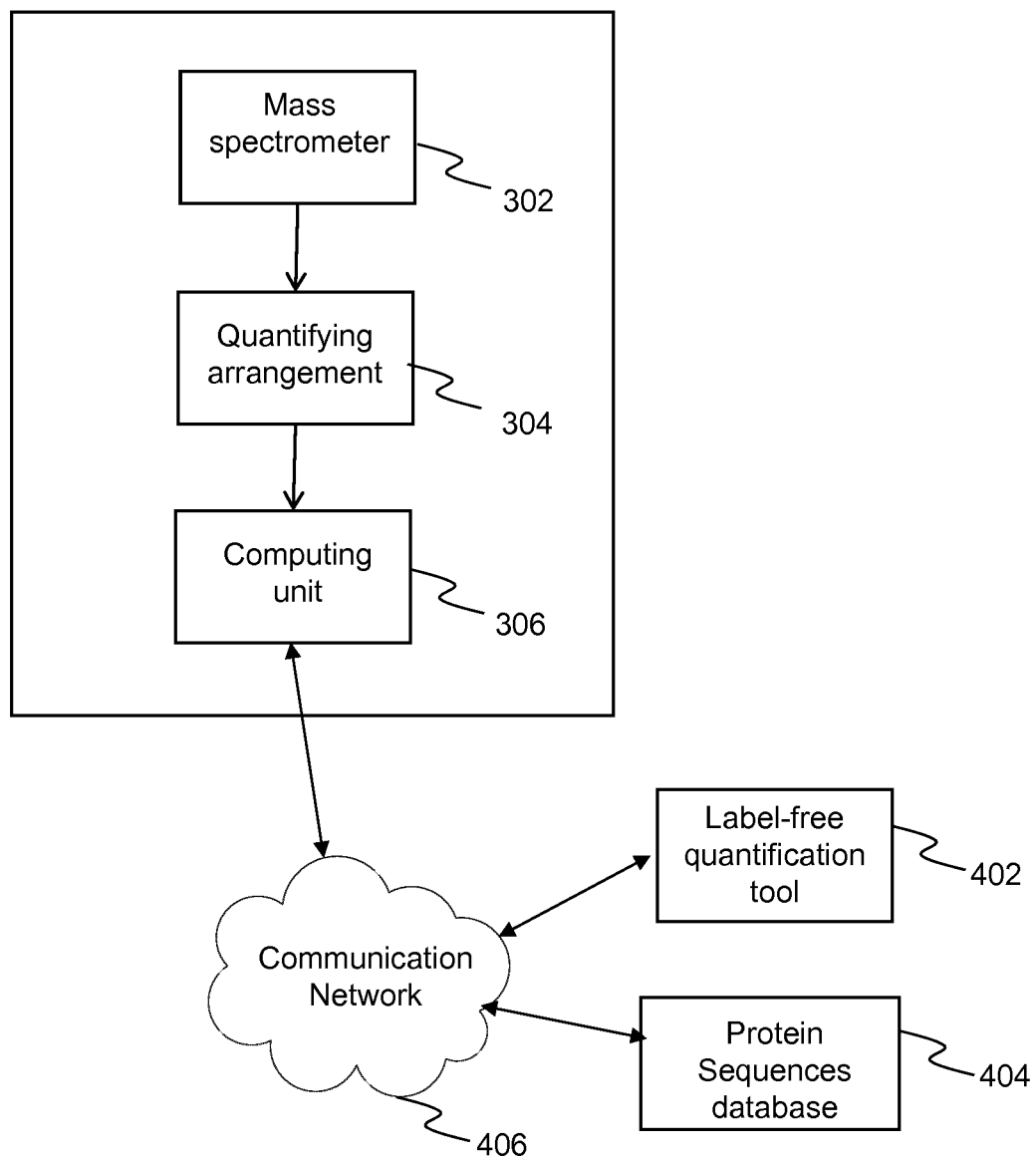
FIG. 4 is a block diagram of a system for identifying biomarkers for breast cancer using healthy plasma and carcinogenic breast tissues, in accordance with another embodiment of the present disclosure.

FIG. 4 is an illustration of a system 400 for identifying biomarkers for breast cancer using healthy plasma and carcinogenic breast tissues, in accordance with an embodiment of the present disclosure. The system 400 is similar to the system 300 of FIG. 3. For example, the system 400 also includes the mass spectrometer 302, the quantifying arrangement 304 and the computing unit 306. However, the computing unit 306 of the system 400 is operationally connected to a Label-free quantification tool 402 and a Protein Sequences database 404 via at least one communication network 406. Furthermore, the Protein Sequences database 404 may include, but is not limited to, MaxQuant® quantification tool with an Andromeda® search engine. Moreover, employing the Label-free quantification tool 402 may include a mass spectrometry analysis of the major disease-specific membrane proteins for obtaining the information relating to the intensity of the major disease-specific membrane proteins.

It will be appreciated that the computing unit 306 of the system 300 may include an inbuilt data associated with the Label-free quantification tool 402 for obtaining intensity information relating to the major disease specific membrane proteins and a Protein Sequences database 404 for searching the recognized disease-specific membrane proteins. However, the Label-free quantification tool 402 and a Protein Sequences database 404 of the system 400 are external server-based arrangements.

In an embodiment, the system 400 further includes the isolating arrangement, and the identifying arrangement. The isolating arrangement of the system 400 may be operable, namely configured, to isolate extracellular vesicles from the tissues of the patient and commented with the identifying arrangement. The identifying arrangement of the system 400 may be operable, namely configured, to identify the membrane proteins associated with the isolated extracellular vesicles.

Figure 5:
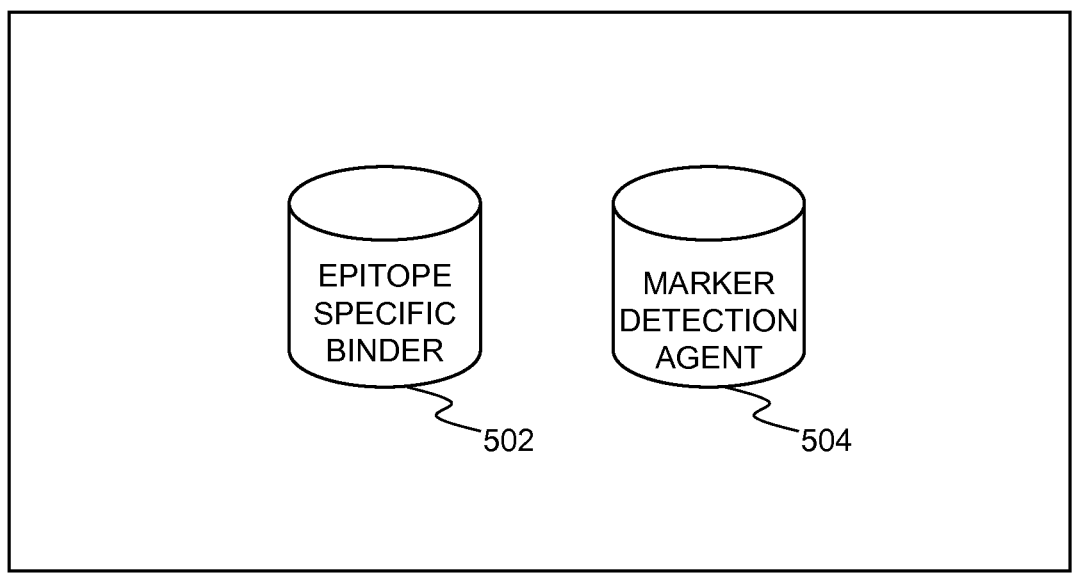
FIG. 5 is a schematic illustration of a kit for capturing extracellular vesicles and detecting breast cancer-associated markers, in accordance with an embodiment of the present disclosure.

FIG. 5 is an illustration of a block diagram of a kit 500 for capturing extracellular vesicles and detecting breast cancer-associated markers namely designed or arranged, for use in conjunction with the methods 100, 200 (shown and described with FIGS. 1 and 2) and the system 300, 400 shown and described with FIGS. 3 and 4). The kit includes an epitope specific binder 502 against breast cancer-associated membrane proteins and at least one breast cancer-associated marker detection agent 504.

The present disclosure further provides a computer program product including non-transitory computer-readable storage medium having computer-readable instructions stored thereon, the computer-readable instructions being executable by a computerized device comprising processing hardware to execute the method 100 of isolating extracellular vesicles from plasma and/or serum and identifying membrane proteins, shown and described with FIG. 1 and the method 200 of identifying breast cancer specific-membrane proteins, shown and described with FIG. 2.

Typically, the isolation of EVs from plasma of healthy tissue involves diluting the tissues collected from the healthy tissues of the individuals, in plasma (e.g. in a range of 10 to 200 ml, 20 to 100 ml, 40 to 80 ml plasma) and centrifuging at for example 10,000 to 20,000×$g_{avg}$ (e.g. Type 70 Ti rotor) for 10 to 60 minutes to pellet down larger EVs. Thereafter, the method typically includes subjecting the supernatant to an ultracentrifugation, typically at 80,000 to 150,000×$g_{avg}$ (Type 70 Ti rotor) for a period of time, typically 1 to 5 hours to pellet down smaller EVs. Both EVs pellets are then resuspended for example in PBS and mixed into one sample and the plasma is layered layering on top of a iodixanol cushion. Thereafter, the method includes centrifuging the cushion and sample at 150,000 to 200,000×$g_{avg}$ (SW 41 Ti rotor) for 0.5 to 5 hours at approximately 4° C. (e.g. 1 to 10° C., e.g. 2-6° C.). The bands are collected and further purified.

Typically the EVs are separated from lipoproteins. EVs are isolated from plasma and/or serum and membrane proteins are identified. The plasma or serum is loaded on top of a density cushion (such as an iodixanol density cushion) and centrifuged. The density cushion allows EVs to float and lipoproteins float on top. The material floating at a density in the range of approximately 1-1.2 g/cm³ (typically 1.06-1.16 g/cm³) of the density cushion and the proteins present in the materials floating at this density are quantified. The concentration of the vesicles in the samples is then increased. The membrane proteins are isolated from the extracellular vesicles and analysed with mass spectrometry for identifying associated membrane proteins.

EVs from cancerous tissues of individuals may be separated by employing a centrifugation based protocol. Typically the method includes slicing of cancerous tissues in fragments and incubating the fragments in for example a RPMI plain medium for 1-60 minutes at 37° C. The incubated fragments are then filtered and the tissue debris are eliminated by centrifugation of the filtered suspension. The centrifuged fragments are again suspended for further purification by centrifugation to collect large vesicles and small vesicles.

The membrane proteins in the protein samples are analysed by spectrometry and they can be further identified and quantified.

EXAMPLES

In the following, the examples of the present disclosure will be described. The examples concern methods of processing sample material, as well as a system that is operable, namely configured, to implement the methods of processing sample material; for example, the system is implemented in a form of a sample processing kit.

Example 1: Isolation of EVs from Plasma of Healthy Tissues

Materials and Method:
The method includes obtaining healthy tissue from a healthy individual. Thereafter, the method includes diluting in a range of 40 ml to 80 ml plasma collected from the healthy tissues of the individuals and centrifuging at 16,500×$g_{avg}$ (Type 70 Ti rotor) for 20 minutes to pellet down larger EVs. Thereafter, the method includes subjecting supernatant to an ultracentrifugation at 118,000×$g_{avg}$ (Type 70 Ti rotor) for 2.5 hours to pellet down smaller EVs. Thereafter, the method includes re-suspending both EVs pellets in PBS and mixing them into one sample with a final volume of 6 ml that is loaded onto an Iodixanol cushion. In particular, the method includes layering 6 ml of plasma on top of a 2 ml 50%, 2 ml 30%, and 2 ml of 10% iodixanol cushion. Thereafter, the method includes centrifuging the cushion and sample at 178,000×$g_{avg}$ (SW 41 Ti rotor) for 2 hours at 4° C. A visible band between the 10% and 30% layer is collected. Furthermore, the method includes adding the collected bands to individual SEC columns. Sepharose CL-2B (GE Healthcare) are packed in a Telos SPE column (Kinesis) to a final volume of 10 ml and equilibrated with PBS. Thereafter, the method includes applying the samples to the premade column, and collecting up to 30 fractions of 0.5 ml with PBS as the elution buffer.

Results:
The method provides EVs present in plasma of the healthy tissues, wherein the EVs may be used for identifying the membrane proteins associated with the isolated extracellular vesicles in the method of isolating extracellular vesicles and identifying membrane proteins therefrom.

Example 2: Sequential Density Gradient and Size Exclusion Chromatography for Separating EVs from Lipoproteins Materials and Method:
The method includes isolating extracellular vesicles from plasma and/or serum and identifying membrane proteins. The method involves working with blood and/or serum samples. Optionally the method includes collecting blood and/or serum. Thereafter, 6 ml of plasma is loaded on top of an iodixanol density cushion and centrifuged. The density cushion allows EVs to float in a density range 1.06-1.16 g/cm³ and lipoproteins float on top of the density cushion due to lower density. Further, materials floating in the density range 1.06-1.16 g/cm³ contain higher concentration of EVs and HDL. Thereafter, the material floating at 1.06-1.16 g/cm³ of the densitycushion are loaded on SEC columns to quantify the proteins present in the materials floating at this density.

Results:
The method provides EVs present in plasma and/or serum, wherein the EVs may be used at the step 108 of the method 100 for purifying the extracellular vesicles by using size exclusion chromatography.

Example 3: Increasing the Concentration of Vesicles

Materials and Method:
The method includes an ultracentrifugation based protocol for increasing the concentration of the EVs derived from the plasma and/or serum. The plasma and/or serum is diluted in PBS and ultra-centrifuged at 16,500×g and 120,000×g, thereafter obtained pellets are dissolved in PBS for loading on top of a density cushion. Thereafter, the density band 1.06-1.16 g/cm³ is further loaded on a SEC column and fractions of extracellular vesicles are collected. The membrane proteins are isolated from the extracellular vesicles and analysed with mass spectrometry for identifying associated membrane proteins.

Results:
The method provides membrane proteins, wherein the membrane proteins may be used in step 204 of the method 200 of identifying breast cancer specific-membrane proteins.

Example 4: Isolation of EVs from Cancerous Tissues

Materials and Method:
The method includes isolating EVs from tissues of individuals by employing a centrifugation based protocol. The method includes slicing of cancerous tissues in fragments of size ranging between 1 mm to 2 mm and incubating the fragments in a RPMI plain medium (Sigma Aldrich) for 30 minutes at 37° C. The RPMI plain medium includes collagenase D (Roche, Basel, Switzerland) (2 mg/ml) and DNase I (Roche) (40 U/ml). The method further includes filtrating incubated fragments with a filter of pore size 70 μm, thereafter the tissue debris are eliminated by centrifugation of the filtered suspension at 300×g for 10 minutes and 2000×g for 20 minutes. The centrifuged fragments are again suspended to centrifugation at 16,500×$g_{avg}$ (Type 45 Ti) for 20 min and 118,000×$g_{avg}$ (Type 45 Ti) for 2.5 hours at 4° C. to collect large vesicles and small vesicles. Thereafter, pellets obtained from centrifugation are re-suspended in PBS. The method further includes combining the large vesicles and small vesicles and purifying the EVs by an isopycnic centrifugation using an iodixanol gradient (OptiPrep™, Sigma-Aldrich). Thereafter, EVs suspended in PBS are mixed with 60% iodixanol and stocked on the bottom of an ultracentrifuge tube followed by an addition of 30% iodixanol again, followed by an addition of 10% iodixanol. Thus, a prepared sample thereby obtained is ultracentrifuged at 100,000×$g_{avg}$ (SW 41 Ti, Beckman Coulter) for 2 hours. The method further includes extracting proteins from EVs and quantifying the extracted proteins by employing Qubit® Protein Assay Kit (Thermo Fisher Scientific).
Results:
The method provides proteins present in the cancerous tissues of individuals, wherein the proteins may be used in identifying the disease-specific membrane proteins in the method 200 of identifying breast cancer specific-membrane proteins.

Example 5: Mass Spectroscopy of the Protein Samples

Materials and Method:
The method includes digesting the protein samples with trypsin using the filter-aided sample preparation (FASP) method. In particular, the EV samples (30 μg) are lysed by the addition of sodium dodecyl sulphate (SDS) to a final concentration of 2% SDS. The method further includes reducing the protein samples with 100 mM dithiothreitol at 60° C. for 30 minutes, transferring the reduced samples on to 30 kDa MWCO Nanosep centrifugal filters (Pall Life Sciences, Ann Arbor, Mich.), washing the filtered sample with 8M urea solution and alkalization of the washed protein samples with 10 mM methyl methanethiosulfonate in 50 mM TEAB and 1% sodium deoxycholate. Thereafter, digestion of protein samples is performed in 50 mM TEAB, 1% sodium deoxycholate at 37° C. in two stages: the samples are incubated with 300 ng of Pierce MS-grade trypsin (Thermo Scientific) for 3 hours, and thereafter the samples are incubated with 300 ng additional trypsin overnight. Furthermore, the method includes desalting digested peptides using Pierce C-18 spin columns (Thermo Scientific), evaporating the solvent and resolving the peptide samples in 3% acetonitrile, 0.1% formic acid solution for LC-MS/MS analysis. Thereafter, each protein sample is analysed on a Q Exactive mass spectrometer (Thermo Fisher Scientific) interfaced with Easy-nLC 1200 nanoflow liquid chromatography system. The peptides are trapped on a Q Exactive mass spectrometer (Thermo Fisher Scientific) interfaced with Easy-nLC 1200 nanoflow liquid chromatography system. Further, the peptides are trapped on the C18 trap column (200 μm×3 cm, particle size 3 μm), and separated on the home-packed C18 analytical column (75 μm×30 cm, particle size 3 μm). Thereafter, precursor ion mass spectra are recorded in positive ion mode at a resolution of 70 000 and a mass range of 400 to 1600 m/z. From recorded precursor ion mass spectra, 10 most intense precursor ions are fragmented using HCD at a collision energy of 30, and MS/MS spectra are recorded in a scan range of 200 to 2000 m/z and a resolution of 35 000.

Results:
The mass spectroscopic analysis of the peptide samples provides the membrane proteins (as listed in Table-1) detectable in breast cancer tissue but not in plasma. The detected membrane proteins may be used in the method 200 of identifying breast cancer specific-membrane proteins.

Example 6: Identification and Label-Free Quantification of Membrane Proteins

Materials and Method:
The method includes quantifying identified proteins by using a MaxQuant® quantification tool in combination with an Andromeda® search engine (version 1.5.2.8) for identification and quantification of membrane proteins. The method includes recognizing disease-specific membrane proteins by searching the membrane proteins on the Andromeda search engine on the basis of at least one parameter including an enzyme specificity, trypsin; a variable modification, an oxidation of methionine (15.995 Da); a fixed modification, carbamidomethylation of cysteine (57.021 Da); two missed cleavages; 20 ppm for precursor ions tolerance and 4.5 ppm for fragment ions tolerance; *Homo sapiens* reference proteome data from Swiss-Prot (20,196 entries); 1% false discovery rate; and a minimum peptide length of seven amino acids. Thereafter, a first major protein is identified and chosen as a representative protein of each protein group. The representative protein is further used for identifying the intensity related information of the disease-specific membrane proteins.

Figure 6:
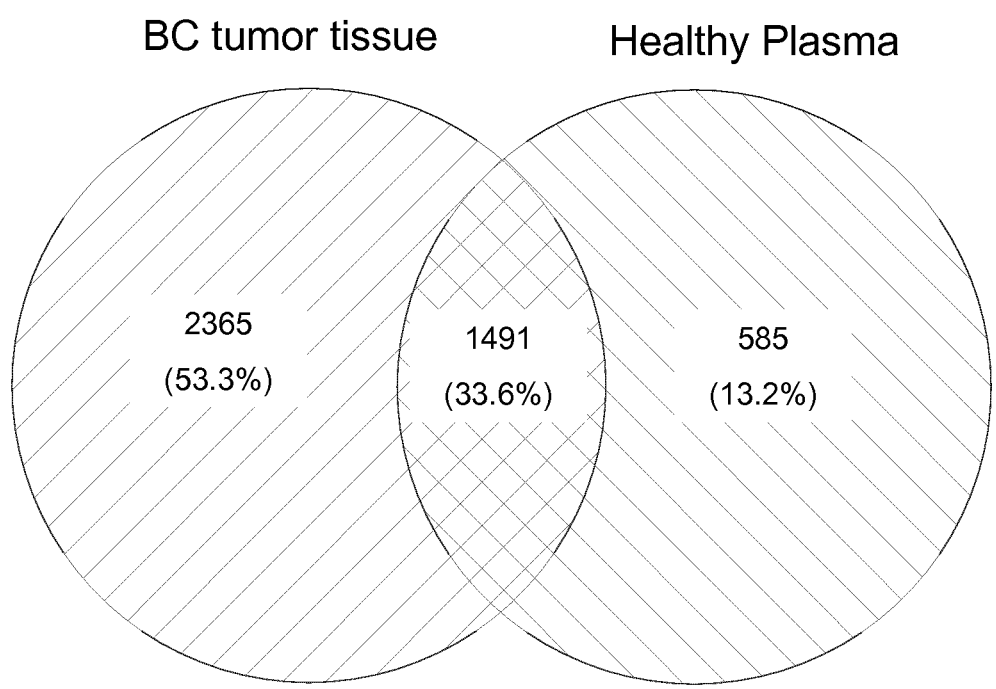
FIG. 6 is a Venn diagram of membrane proteins found in human breast cancer tissues by mass spectrometry against all proteins found in the plasma proteomics, in accordance with an embodiment of the present disclosure

Results:
Identification and Label-free Quantification of membrane proteins provide the major disease-specific membrane proteins for each group of the recognized disease-specific membrane proteins. The major disease-specific membrane proteins may be used in the method 200 of identifying breast cancer specific-membrane proteins. As shown in FIG. 6, there are 15.9% similar proteins present in breast cancer tissues and healthy tissue.

Example 7: NanoFCM Analysis of the Membrane Proteins

Materials and Method:
The method includes profiling of membrane proteins derived from EVs. The membrane proteins derived from EVs are analysed with nanoFCM. Furthermore, the nanoFCM analysis includes detecting single particles similar to FACS. In particular, the EVs derived from the tissues are incubated with either of PE conjugated CD81 or CD47 antibodies for 30 minutes at 37 C. Thereafter, the method includes recovering the EVs by ultracentrifugation at 100,000×$g_{avg}$ (Type120.1) for 15 minutes and recovered EVs are re-suspended with PBS. The stained EV's are subjected to nanoFCM analysis for identifying PE signals for single EV. Thereafter, tissue derived plasma EVs are used as control for overlapping the PE signals for various EVs and detecting biomarker in membrane proteins of the EVs of the patient.

Figure 7A:
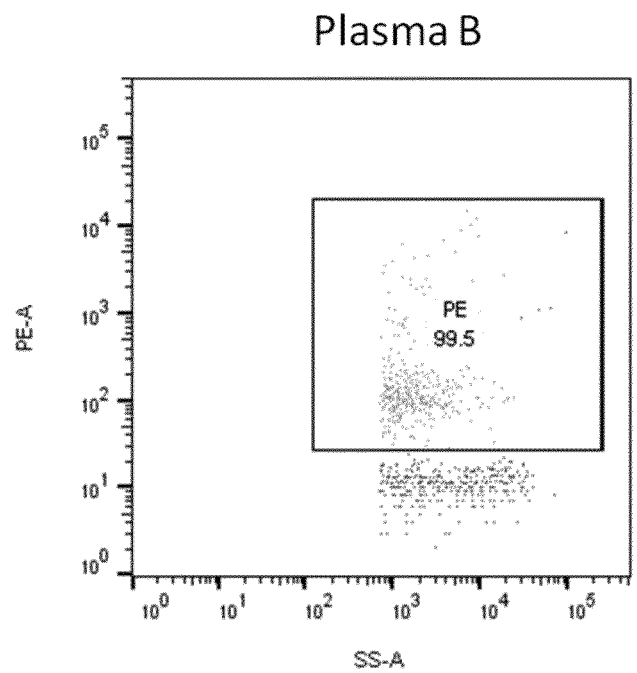
FIGS. 7A-7B are graphical representations of expression of CD47 on Plasma-Extracellular vesicles, in accordance with an embodiment of the present disclosure.
Figure 7B:
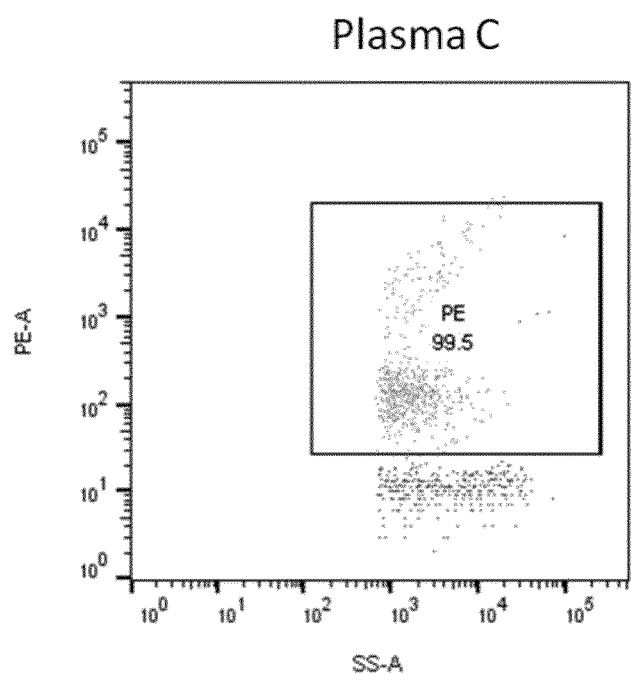
Figure 8A:
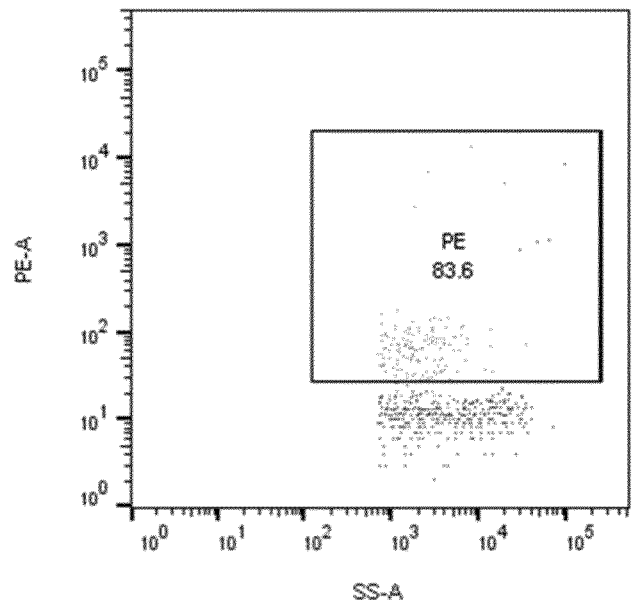
FIGS. 8A-8B are graphical representations of expression of CD81 on Plasma-Extracellular vesicles, in accordance with an embodiment of the present disclosure.
Figure 8B:
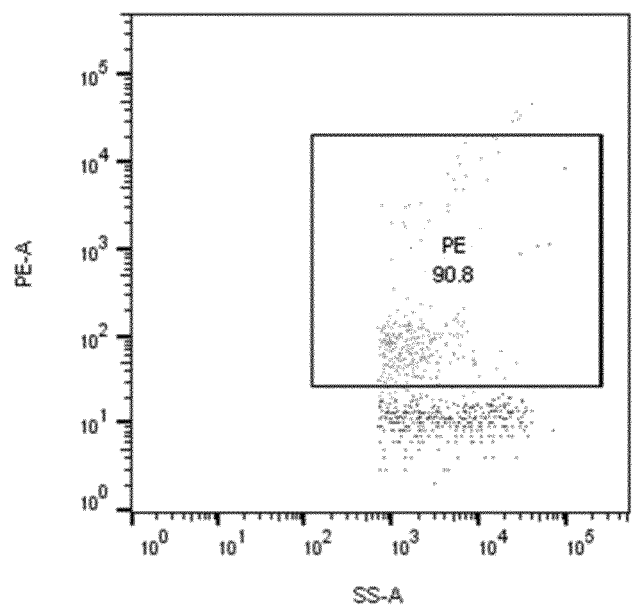
Figure 9A:
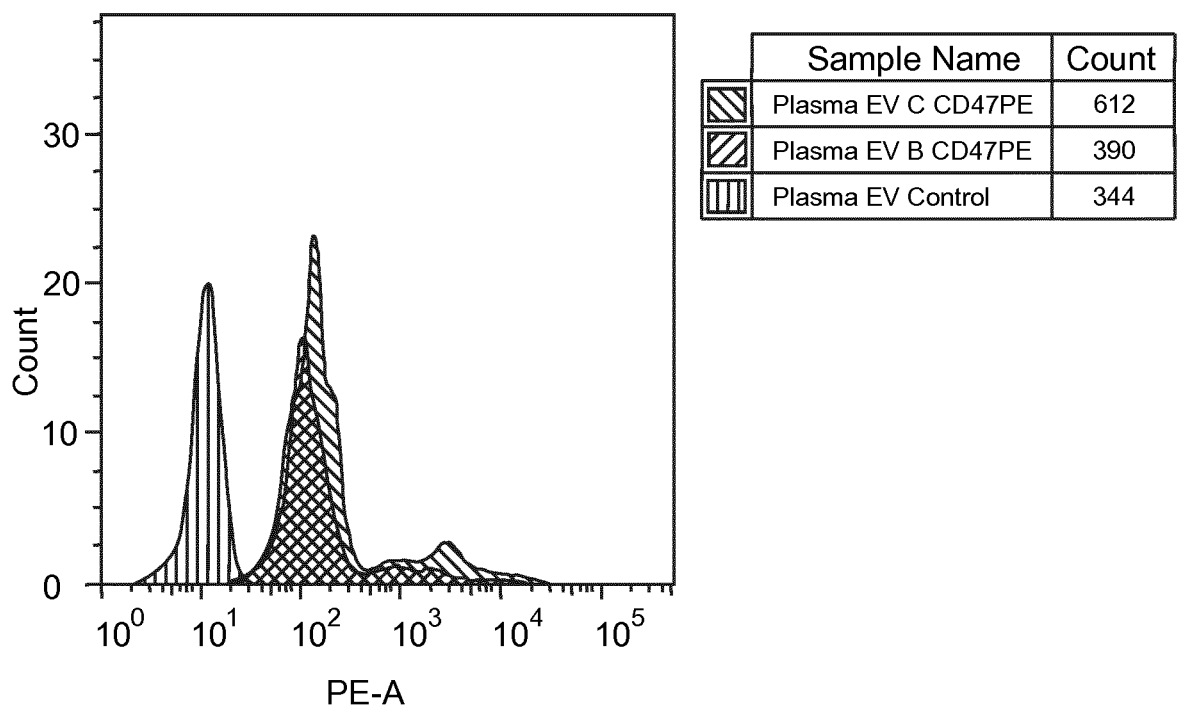
FIGS. 9A-9B are graphical representation of expression of CD47 and CD81 on Plasma-Extracellular vesicles in accordance with an embodiment of the present disclosure.
Figure 9B:
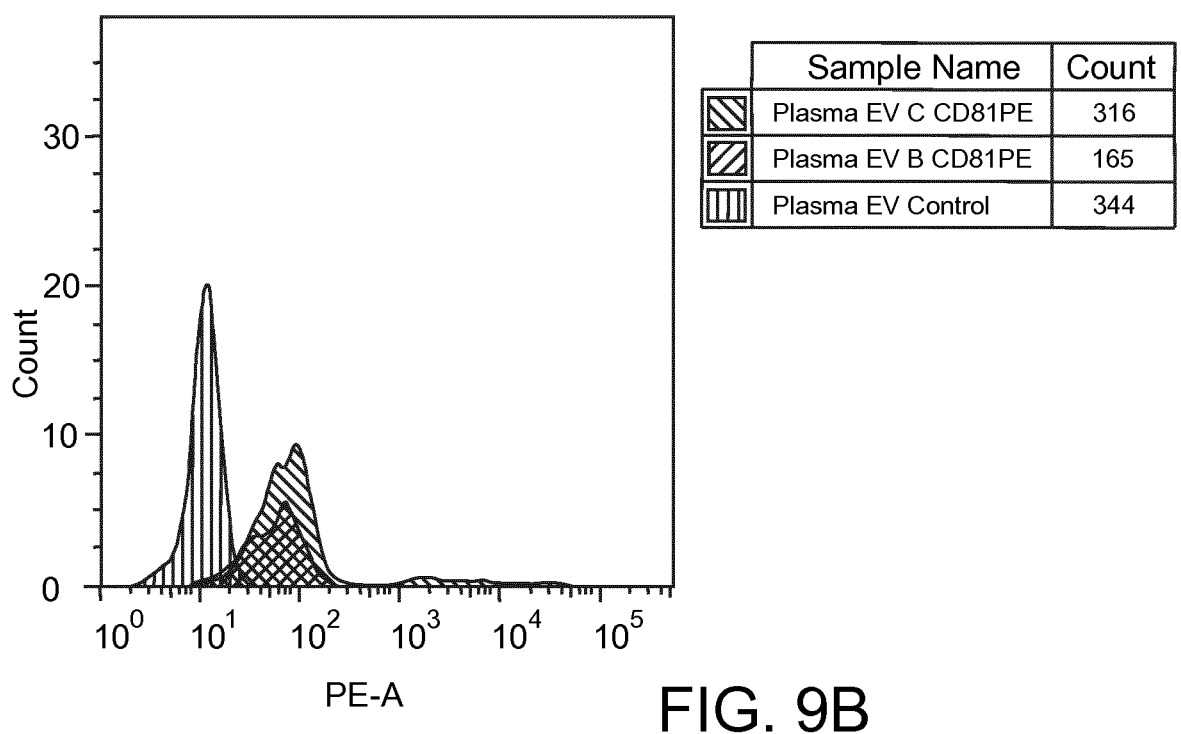

Results:
As shown in FIGS. 7A-7B, PE signals of PE conjugated CD47 antibodies for two different EVs samples (Plasma B and Plasma C) are identical. For PE conjugated CD47 antibody in both plasma B and plasma C refers to identical overlapping concentration in respect to control sample plasma A. Moreover, as shown in FIGS. 8A-8B PE Signals of PE conjugated CD81 antibodies for the plasma B and the plasma C samples in respect to control sample plasma A have different overlapping concentration. For PE conjugated CD81 antibodies the plasma B sample has lesser intensity than the plasma C sample. Therefore, the plasma EVs harbor CD81 and CD47 on their surface. Furthermore, as shown in FIGS. 9A-9B, overlapping the findings of nanoFCM analysis for the control sample plasma A, the plasma B and the plasma C results in higher count for PE conjugated CD81 antibodies.

APPENDIX TO THE SPECIFICATION

TABLE 1

| Uniprot ID | Protein names | Primary localization |
| --- | --- | --- |
| Q5ZPR3 | CD276 antigen | Membrane |
| Q14108 | Lysosome membrane protein 2 | Lysosome membrane |
| Q07954 | Prolow-density lipoprotein receptor-related protein 1 | Cell membrane |
| P29992 | Guanine nucleotide-binding protein subunit alpha-11 | Cell membrane |
| P30504 | HLA class I histocompatibility antigen, Cw-4 alpha chain | Membrane |
| P16144 | Integrin beta-4 | Cell membrane |
| Q07000 | HLA class I histocompatibility antigen, Cw-15 alpha chain | Membrane |
| Q01814 | Plasma membrane calcium-transporting ATPase 2 | Cell junction |
| P21397 | Amine oxidase [flavin-containing] A | Mitochondrion outer membrane |
| P43353 | Aldehyde dehydrogenase family 3 member B1 | Cell membrane |
| Q16651 | Prostasin | Cell membrane |
| P05026 | Sodium/potassium-transporting ATPase subunit beta-1 | Cell membrane |
| P09758 | Tumor-associated calcium signal transducer 2 | Membrane |
| P00533 | Epidermal growth factor receptor | Cell membrane |
| Q03113 | Guanine nucleotide-binding protein subunit alpha-12 | Membrane |
| Q9UBG0 | C-type mannose receptor 2 | Membrane |
| P21589 | 5'-nucleotidase | Cell membrane |
| P30457 | HLA class I histocompatibility antigen, A-66 alpha chain | Membrane |
| Q9P2B2 | Prostaglandin F2 receptor negative regulator | Endoplasmic reticulum membrane |
| P30466 | HLA class I histocompatibility antigen, B-18 alpha chain | Membrane |
| P49961 | Ectonucleoside triphosphate diphosphohydrolase 1 | Membrane |
| P04626 | Receptor tyrosine-protein kinase erbB-2 | Cell membrane |
| P16190 | HLA class I histocompatibility antigen, A-33 alpha chain | Membrane |
| P09619 | Platelet-derived growth factor receptor beta | Cell membrane |
| Q07065 | Cytoskeleton-associated protein 4 | Endoplasmic reticulum membrane |
| P54760 | Ephrin type-B receptor 4 | Cell membrane |
| Q29963 | HLA class I histocompatibility antigen, Cw-6 alpha chain | Membrane |
| Q92896 | Golgi apparatus protein 1 | Golgi apparatus membrane |
| Q9UGT4 | Sushi domain-containing protein 2 | Cell membrane |
| Q9NZM1 | Myoferlin | Cell membrane |
| P10321 | HLA class I histocompatibility antigen, Cw-7 alpha chain | Membrane |
| P10319 | HLA class I histocompatibility antigen, B-58 alpha chain | Membrane |
| Q92629 | Delta-sarcoglycan | Cell membrane |
| Q13277 | Syntaxin-3 | Membrane |
| P08473 | Neprilysin | Cell membrane |
| Q9UBI6 | Guanine nucleotide-binding protein G | Cell membrane |
| Q9ULC3 | Ras-related protein Rab-23 | Cell membrane |
| O43520 | Phospholipid-transporting ATPase IC | Cell membrane |
| P17693 | HLA class I histocompatibility antigen, alpha chain G | Membrane |
| Q969E2 | Secretory carrier-associated membrane protein 4 | Membrane |
| P04439 | HLA class I histocompatibility antigen, A-3 alpha chain | Membrane |
| O95716 | Ras-related protein Rab-3D | Cell membrane |
| P60059 | Protein transport protein Sec61 subunit gamma | Endoplasmic reticulum membrane |
| Q16853 | Membrane primary amine oxidase | Cell membrane |
| P54753 | Ephrin type-B receptor 3 | Cell membrane |
| P56199 | Integrin alpha-1 | Membrane |
| P09471 | Guanine nucleotide-binding protein G | Cell membrane |

TABLE 1-continued

| Uniprot ID | Protein names | Primary localization |
|---|---|---|
| P07099 | Epoxide hydrolase 1 | Microsome membrane |
| O75781 | Paralemmin-1 | Cell membrane |
| P01891 | HLA class I histocompatibility antigen, A-68 alpha chain | Membrane |
| P36269 | Gamma-glutamyltransferase 5 | Membrane |
| Q8WVQ1 | Soluble calcium-activated nucleotidase 1 | Endoplasmic reticulum membrane |
| Q6ZMG9 | Ceramide synthase 6 | Nucleus membrane |
| P22413 | Ectonucleotide pyrophosphatase/phosphodiesterase family member 1 | Cell membrane |
| P0CG08 | Golgi pH regulator B | Golgi apparatus membrane |
| Q9C0D9 | Ethanolaminephosphotransferase 1 | Membrane |
| O95070 | Protein YIF1A | Endoplasmic reticulum membrane |
| O94923 | D-glucuronyl C5-epimerase | Golgi apparatus membrane |
| Q9NXS2 | Glutaminyl-peptide cyclotransferase-like protein | Golgi apparatus membrane |
| Q9UL01 | Dermatan-sulfate epimerase | Membrane |
| P01911 | HLA class II histocompatibility antigen, DRB1-15 beta chain | Cell membrane |
| Q8TED1 | Probable glutathione peroxidase 8 | Membrane |
| P78382 | CMP-sialic acid transporter | Golgi apparatus membrane |
| P08571 | Monocyte differentiation antigen CD14 | Cell membrane |
| Q9Y6A9 | Signal peptidase complex subunit 1 | Microsome membrane |
| P54289 | Voltage-dependent calcium channel subunit alpha-2/delta-1 | Membrane |
| P78536 | Disintegrin and metalloproteinase domain-containing protein 17 | Membrane |
| Q9NYL4 | Peptidyl-prolyl cis-trans isomerase FKBP11 | Membrane |
| Q30154 | HLA class II histocompatibility antigen, DR beta 5 chain | Cell membrane |
| P12235 | ADP/ATP translocase 1 | Mitochondrion inner membrane |
| O00391 | Sulfhydryl oxidase 1 | Golgi apparatus membrane |
| Q96S52 | GPI transamidase component PIG-S | Endoplasmic reticulum membrane |
| Q15155 | Nodal modulator 1 | Membrane |
| O14786 | Neuropilin-1 | Cell membrane |
| Q8TF66 | Leucine-rich repeat-containing protein 15 | Membrane |
| Q13724 | Mannosyl-oligosaccharide glucosidase | Endoplasmic reticulum membrane |
| Q9H920 | RING finger protein 121 | Membrane |
| P20039 | HLA class II histocompatibility antigen, DRB1-11 beta chain | Cell membrane |
| Q9BUN8 | Derlin-1 | Endoplasmic reticulum membrane |
| O94901 | SUN domain-containing protein 1 | Nucleus inner membrane |
| P01920 | HLA class II histocompatibility antigen, DQ beta 1 chain | Cell membrane |
| P79483 | HLA class II histocompatibility antigen, DR beta 3 chain | Cell membrane |
| Q6P4E1 | Protein CASC4 | Membrane |
| P11717 | Cation-independent mannose-6-phosphate receptor | Lysosome membrane |
| Q4V9L6 | Transmembrane protein 119 | Cell membrane |
| Q13641 | Trophoblast glycoprotein | Cell membrane |
| P04440 | HLA class II histocompatibility antigen, DP beta 1 chain | Cell membrane |
| P00167 | Cytochrome b5 | Endoplasmic reticulum membrane |
| P29323 | Ephrin type-B receptor 2 | Cell membrane |
| Q6UW68 | Transmembrane protein 205 | Membrane |
| Q12884 | Prolyl endopeptidase FAP | Cell surface |
| P13761 | HLA class II histocompatibility antigen, DRB1-7 beta chain | Cell membrane |
| Q96GQ5 | RUS1 family protein C16orf58 | Membrane |
| Q9UH99 | SUN domain-containing protein 2 | Nucleus inner membrane |

TABLE 1-continued

| Uniprot ID | Protein names | Primary localization |
|---|---|---|
| Q9BV10 | Dol-P-Man: Man | Endoplasmic reticulum membrane |
| O75110 | Probable phospholipid-transporting ATPase IIA | Early endosome membrane |
| P05362 | Intercellular adhesion molecule 1 | Membrane |
| P01912 | HLA class II histocompatibility antigen, DRB1-3 chain | Cell membrane |
| Q9NZ01 | Very-long-chain enoyl-CoA reductase | Endoplasmic reticulum membrane |
| Q9HBR0 | Putative sodium-coupled neutral amino acid transporter 10 | Membrane |
| P04233 | HLA class II histocompatibility antigen gamma chain | Cell membrane |
| O15321 | Transmembrane 9 superfamily member 1 | Lysosome membrane |
| Q9UIW2 | Plexin-A1 | Cell membrane |
| P04216 | Thy-1 membrane glycoprotein | Cell membrane |
| Q10469 | Alpha-1,6-mannosyl-glycoprotein 2-beta-N-acetylglucosaminyltransferase | Golgi apparatus membrane |
| Q30134 | HLA class II histocompatibility antigen, DRB1-8 beta chain | Cell membrane |
| Q13308 | Inactive tyrosine-protein kinase 7 | Membrane |
| P50281 | Matrix metalloproteinase-14 | Membrane |
| Q92643 | GPI-anchor transamidase | Endoplasmic reticulum membrane |
| Q8WZA1 | Protein O-linked-mannose beta-1,2-N-acetylglucosaminyltransferase 1 | Golgi apparatus membrane |
| Q8IZA0 | Dyslexia-associated protein KIAA0319-like protein | Cytoplasmic granule membrane |
| O75923 | Dysferlin | Cell membrane |
| Q13740 | CD166 antigen | Cell membrane |
| Q9NYP7 | Elongation of very long chain fatty acids protein 5 | Endoplasmic reticulum membrane |
| Q9GZM5 | Protein YIPF3 | Cell membrane |
| P61313 | 60S ribosomal protein L15 | Membrane |
| P13760 | HLA class II histocompatibility antigen, DRB1-4 beta chain | Cell membrane |
| Q5Y7A7 | HLA class II histocompatibility antigen, DRB1-13 beta chain | Cell membrane |
| O60476 | Mannosyl-oligosaccharide 1,2-alpha-mannosidase IB | Golgi apparatus membrane |
| P06213 | Insulin receptor | Cell membrane |
| Q9TQE0 | HLA class II histocompatibility antigen, DRB1-9 beta chain | Cell membrane |
| O60449 | Lymphocyte antigen 75 | Membrane |
| P20036 | HLA class II histocompatibility antigen, DP alpha 1 chain | Cell membrane |
| O75976 | Carboxypeptidase D | Cell membrane |
| Q14573 | Inositol 1,4,5-trisphosphate receptor type 3 | Endoplasmic reticulum membrane |
| Q969L2 | Protein MAL2 | Cell membrane |
| Q92673 | Sortilin-related receptor | Membrane |
| P19440 | Gamma-glutamyltranspeptidase 1 | Cell membrane |
| Q99828 | Calcium and integrin-binding protein 1 | Membrane |
| Q8N271 | Prominin-2 | Apical cell membrane |
| P11215 | Integrin alpha-M | Membrane |
| O60486 | Plexin-C1 | Membrane |
| P08582 | Melanotransferrin | Cell membrane |
| P43121 | Cell surface glycoprotein MUC18 | Membrane |
| Q9NQ84 | G-protein coupled receptor family C group 5 member C | Cell membrane |
| P12830 | Cadherin-1 | Cell junction |
| Q15758 | Neutral amino acid transporter B | Cell membrane |
| Q9BXP2 | Solute carrier family 12 member 9 | Cell membrane |
| O43759 | Synaptogyrin-1 | Membrane |
| O43292 | Glycosylphosphatidylinositol anchor attachment 1 protein | Endoplasmic reticulum membrane |
| Q9Y320 | Thioredoxin-related transmembrane protein 2 | Membrane |
| Q8N4A0 | Polypeptide N-acetylgalactosaminyltransferase 4 | Golgi apparatus membrane |
| Q16850 | Lanosterol 14-alpha demethylase | Endoplasmic reticulum membrane |
| Q8WUD6 | Cholinephosphotransferase 1 | Golgi apparatus membrane |
| Q6UWJ1 | Transmembrane and coiled-coil domain-containing protein 3 | Membrane |
| Q6PCB7 | Long-chain fatty acid transport protein 1 | Cell membrane |

TABLE 1-continued

| Uniprot ID | Protein names | Primary localization |
|---|---|---|
| Q6ZXV5 | Transmembrane and TPR repeat-containing protein 3 | Membrane |
| Q14126 | Desmoglein-2 | Cell membrane |
| P15941 | Mucin-1 | Apical cell membrane |
| O14683 | Tumor protein p53-inducible protein 11 | Membrane |
| Q68CQ7 | Glycosyltransferase 8 domain-containing protein 1 | Membrane |
| Q07075 | Glutamyl aminopeptidase | Membrane |
| Q16585 | Beta-sarcoglycan | Cell membrane |
| Q9H3S5 | GPI mannosyltransferase 1 | Endoplasmic reticulum membrane |
| Q92633 | Lysophosphatidic acid receptor 1 | Cell surface |
| O75063 | Glycosaminoglycan xylosylkinase | Golgi apparatus membrane |
| Q9UKM7 | Endoplasmic reticulum mannosyl-oligosaccharide 1,2-alpha-mannosidase | Endoplasmic reticulum membrane |
| P25445 | Tumor necrosis factor receptor superfamily member 6 | Cell membrane |
| P52569 | Cationic amino acid transporter 2 | Cell membrane |
| Q9H0V1 | Transmembrane protein 168 | Membrane |
| Q06136 | 3-ketodihydrosphingosine reductase | Endoplasmic reticulum membrane |
| O76062 | Delta | Microsome membrane |
| Q8NCL4 | Polypeptide N-acetylgalactosaminyltransferase 6 | Golgi apparatus membrane |
| Q6UXY8 | Transmembrane channel-like protein 5 | Membrane |
| Q5KU26 | Collectin-12 | Membrane |
| O00478 | Butyrophilin subfamily 3 member A3 | Cell membrane |
| Q9H1C3 | Glycosyltransferase 8 domain-containing protein 2 | Membrane |
| P26006 | Integrin alpha-3 | Cell membrane |
| Q5H8A4 | GPI ethanolamine phosphate transferase 2 | Endoplasmic reticulum membrane |
| Q6UXG2 | UPF0577 protein KIAA1324 | Cell membrane |
| Q04912 | Macrophage-stimulating protein receptor | Membrane |
| Q5VW32 | BRO1 domain-containing protein BROX | Membrane |
| O95470 | Sphingosine-1-phosphate lyase 1 | Endoplasmic reticulum membrane |
| Q13332 | Receptor-type tyrosine-protein phosphatase S | Membrane |
| P18564 | Integrin beta-6 | Membrane |
| Q9H490 | Phosphatidylinositol glycan anchor biosynthesis class U protein | Endoplasmic reticulum membrane |
| Q9NY15 | Stabilin-1 | Membrane |
| Q14714 | Sarcospan | Cell membrane |
| Q7Z3B1 | Neuronal growth regulator 1 | Cell membrane |
| Q8N139 | ATP-binding cassette sub-family A member 6 | Membrane |
| Q687X5 | Metalloreductase STEAP4 | Cell membrane |
| Q9Y241 | HIG1 domain family member 1A, mitochondrial | Mitochondrion membrane |
| Q9P0I2 | ER membrane protein complex subunit 3 | Membrane |
| Q9Y5Y0 | Feline leukemia virus subgroup C receptor-related protein 1 | Cell membrane |
| Q8NBN3 | Transmembrane protein 87A | Membrane |
| P20702 | Integrin alpha-X | Membrane |
| Q9ULG6 | Cell cycle progression protein 1 | Cytoplasmic granule membrane |
| Q6UWH4 | Protein FAM198B | Golgi apparatus membrane |
| O75354 | Ectonucleoside triphosphate diphosphohydrolase 6 | Golgi apparatus membrane |
| P18827 | Syndecan-1 | Membrane |
| P55061 | Bax inhibitor 1 | Endoplasmic reticulum membrane |
| Q9Y666 | Solute carrier family 12 member 7 | Cell membrane |
| Q9UM00 | Calcium load-activated calcium channel | Endoplasmic reticulum membrane |
| Q86SF2 | N-acetylgalactosaminyltransferase 7 | Golgi apparatus membrane |
| P59768 | Guanine nucleotide-binding protein G | Cell membrane |
| P37268 | Squalene synthase | Endoplasmic reticulum membrane |
| O15270 | Serine palmitoyltransferase 2 | Endoplasmic reticulum membrane |
| P43007 | Neutral amino acid transporter A | Membrane |
| Q5BJF2 | Transmembrane protein 97 | Nucleus membrane |
| Q68DH5 | LMBR1 domain-containing protein 2 | Membrane |

TABLE 1-continued

| Uniprot ID | Protein names | Primary localization |
|---|---|---|
| Q9H8Y8 | Golgi reassembly-stacking protein 2 membrane | Golgi apparatus |
| O14569 | Cytochrome b561 domain-containing protein 2 | Membrane |
| P30511 | HLA class I histocompatibility antigen, alpha chain F | Membrane |
| Q13488 | V-type proton ATPase 116 kDa subunit a isoform 3 | Membrane |
| Q9UM21 | Alpha-1,3-mannosyl-glycoprotein 4-beta-N-acetylglucosaminyltransferase A | Golgi apparatus membrane |
| Q9H9S5 | Fukutin-related protein | Golgi apparatus membrane |
| O43826 | Glucose-6-phosphate exchanger SLC37A4 | Endoplasmic reticulum membrane |
| P27449 | V-type proton ATPase 16 kDa proteolipid subunit | Vacuole membrane |
| Q9BZZ2 | Sialoadhesin | Cell membrane |
| Q8NCH0 | Carbohydrate sulfotransferase 14 | Golgi apparatus membrane |
| P20701 | Integrin alpha-L | Cell membrane |
| O15440 | Multidrug resistance-associated protein 5 | Membrane |
| Q8NFJ5 | Retinoic acid-induced protein 3 | Cell membrane |
| Q96J66 | ATP-binding cassette sub-family C member 11 | Cell membrane |

The invention claimed is:

1. A method of identifying tumor tissue specific-membrane proteins, the method comprising steps of:
   (a) isolating extracellular vesicles from a tumor tissue of patients, the isolating comprising:
      (i) fragmenting the tissue;
      (ii) incubating the fragmented tissue with one or more enzymes to release the extracellular vesicles, wherein the one or more enzymes are selected from a group of proteases including a matrix metalloproteinase, collagenases, and papain and nucleases including DNase, RNase, and Benzonase; and
      (iii) separating tissue debris and the extracellular vesicles;
   (b) identifying membrane proteins associated with the isolated extracellular vesicles by mass spectrometry;
   (c) comparing membrane proteins identified in step (b) with membrane proteins identified as associated with extracellular vesicles isolated from plasma and/or serum sample of healthy subjects by specifically subtracting the membrane proteins identified as associated with extracellular vesicles isolated from plasma and/or serum sample of healthy subjects, to identify tumor tissue-specific membrane proteins; and
   (d) creating membrane proteins profiles for the identified tumor tissue-specific membrane proteins.

2. The method of claim 1, wherein the membrane proteins are identified as associated with extracellular vesicles isolated from plasma and/or serum sample of healthy subjects by a method comprising:
   (i) providing human plasma and/or serum;
   (ii) separating lipoproteins and extracellular vesicles from the human plasma and/or serum by a density gradient preparation;
   (iii) collecting the extracellular vesicles from the separated lipoproteins and extracellular vesicles;
   (iv) isolating and purifying the collected extracellular vesicles by using size exclusion chromatography;
   (v) treating the isolated and purified extracellular vesicles with an aqueous solution to obtain membranes of the extracellular vesicles, wherein the aqueous solution has a pH in a range of 9 to 14;
   (vi) adding salt in a concentration range between 0.5-2.0M to the aqueous solution;
   (vii) isolating the membranes from the treated extracellular vesicles; and
   (viii) identifying proteins on the isolated membranes by employing mass spectrometry.

3. The method of claim 2, further comprising (ix) ultracentrifugation of the human plasma and/or serum to concentrate extracellular vesicles therein, wherein the step (ix) is performed before the step (ii).

4. The method of claim 1, further comprising plotting the created membrane proteins profiles of the patient against pre-determined membrane proteins profiles of healthy tissues and cancerous tissues.

5. The method of claim 4, wherein the plotting comprises employing at least one of a nanoFCM analysis, ELISA, alphaLISA, FACS, fluorescent correlation microscopy and immune-electron microscopy.

6. The method of claim 1, wherein the tumor tissue is breast cancer tissue.

7. The method of claim 6, further comprising plotting the created membrane proteins profiles of the patient against pre-determined membrane proteins profiles of healthy and cancerous breast tissue.

8. The method of claim 7, wherein breast cancer-specific membrane protein is Receptor tyrosine-protein kinase erbB-2 and/or Cytoskeleton-associated protein 4.

9. A computer program product comprising non-transitory computer-readable storage medium having computer-readable instructions stored thereon, the computer-readable instructions being executable by a computerized device comprising processing hardware to execute a method of identifying tumor tissue specific-membrane proteins, the method comprising steps of:
   (a) isolating extracellular vesicles from a tumor tissue of patients, the isolating comprising:
      (i) fragmenting the tissue;
      (ii) incubating the fragmented tissue with one or more enzymes to release the extracellular vesicles, wherein the one or more enzymes are selected from a group of proteases including a matrix metalloproteinase, collagenases, and papain and nucleases including DNase, RNase, and Benzonase; and (iii) separating tissue debris and the extracellular vesicles;

(b) identifying membrane proteins associated with the isolated extracellular vesicles by mass spectrometry;

(c) comparing membrane proteins identified in step (b) with membrane proteins identified as associated with extracellular vesicles isolated from plasma and/or serum sample of healthy subjects by specifically subtracting the membrane proteins identified as associated with extracellular vesicles isolated from plasma and/or serum sample of healthy subjects, to identify tumor tissue-specific membrane proteins; and (d) creating membrane proteins profiles for the identified tumor tissue-specific membrane proteins.

10. The method of claim 7, wherein the plotting comprises employing at least one of a nanoFCM analysis, ELISA, alphaLISA, FACS, fluorescent correlation microscopy and immune-electron microscopy.

11. The method of claim 1, wherein separating tissue debris and the extracellular vesicles comprises centrifugation.

* * * * *